United States Patent [19]

Grabiak et al.

[11]  4,319,913
[45]  Mar. 16, 1982

[54] SUBSTITUTED BENZAZAPHOSPHOLES, HERBICIDAL COMPOSITIONS AND THE USE THEREOF

[75] Inventors: Raymond C. Grabiak, Creve Coeur; James A. Miles, Olivette, both of Mo.

[73] Assignee: Monsanto Company, St. Louis, Mo.

[21] Appl. No.: 119,051

[22] Filed: Feb. 25, 1980

Related U.S. Application Data

[63] Continuation-in-part of Ser. No. 55,431, Jul. 6, 1979, abandoned.

[51] Int. Cl.$^3$ .................. A01N 57/36; C07F 9/65
[52] U.S. Cl. ........................... 71/86; 556/404; 564/13
[58] Field of Search ............... 71/86; 564/13; 556/404

[56] References Cited

U.S. PATENT DOCUMENTS

| | | | |
|---|---|---|---|
| 3,449,426 | 6/1969 | Braye | 71/86 X |
| 3,980,618 | 9/1976 | Birum | 260/551 P |
| 4,102,949 | 7/1978 | Schliebs et al. | 260/985 |

OTHER PUBLICATIONS

Collins et al., Aust. J. Chem., 27, 1759–1765 (1974).
Dennis et al., J. Am. Chem. Soc., 88, 3431–3432 (1966).
Dannley et al., J. Org. Chem., 26, 3995–3998 (1961).
Ludt et al., J. Org. Chem., 36, 1607–1613 (1971).
Hellwinkel et al., Tetrahedron Letters, No. 37, 3241–3244 (1977).
Eberhard et al., J. Am. Chem. Soc., 87, 253–260 (1977).
Walborsky et al., J. Org. Chem., 43, 731–734 (1978).
Miles et al., J. Org. Chem, 43, 4668–4670 (1978).
Walborsky et al., Chemical Abstracts, vol. 88, 89736g (04/78).
Lopez et al., Chemical Abstracts, vol. 75, 49232q (1971).

Primary Examiner—Anton H. Sutto
Assistant Examiner—Diana G. Rivers
Attorney, Agent, or Firm—Patricia A. Coburn; Donald W. Peterson

[57] ABSTRACT

This disclosure relates to novel substituted benzazaphospholes and to methods of preparing such compounds. This invention further relates to herbicidal compositions containing such benzazaphospholes and to herbicidal methods employing such compounds and compositions. The compounds of the present invention are members of a class of bicyclic hetero compounds containing only one phosphorus-nitrogen bond and different moieties bonded to the phosphorus and nitrogen.

22 Claims, No Drawings

SUBSTITUTED BENZAZAPHOSPHOLES, HERBICIDAL COMPOSITIONS AND THE USE THEREOF

This application is a continuation-in-part of application Ser. No. 55,431; filed July 6, 1979, now abandoned.

This invention relates to novel substituted benzazaphospholes and to methods of preparing such compounds. This invention further relates to herbicidal compositions containing such benzazaphospholes and to herbicidal methods employing such compounds and compositions. The compounds of the present invention are members of a class of bicyclic hetero compounds containing only one phosphorus-nitrogen bond and different moieties bonded to the phosphorus and nitrogen.

The compounds of the present invention are represented by the formula

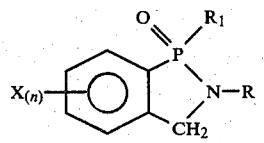  (I)

wherein R is selected from the group consisting of hydrogen, $C_1$-$C_8$ alkyl, benzyl, trimethylsilyl, phenyl, phenoxyphenyl, a

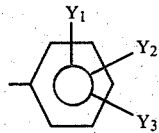

group, wherein $Y_1$ is selected from the group consisting of $C_1$-$C_4$ alkyl, $C_1$-$C_4$ alkoxy, $C_1$-$C_4$ haloalkyl, nitro and halogen and $Y_2$ and $Y_3$ are independently either hydrogen or selected from the group represented by $Y_1$, and substituted carbonyl of the formula

wherein $R_2$ is selected from the group consisting of $C_1$-$C_4$ alkoxy, $C_1$-$C_4$ haloalkyl and $C_1$-$C_4$ alkylamino; $R_1$ is selected from the group consisting of $C_1$-$C_8$ alkyl, $C_3$-$C_8$ cycloalkyl, phenyl, biphenyl, phenoxyphenyl and a

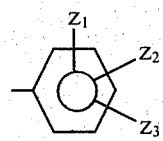

group, wherein $Z_1$ is selected from the group consisting of $C_1$-$C_4$ alkyl, $C_1$-$C_4$ alkoxy, $C_1$-$C_4$ alkylthio, $C_1$-$C_4$ dialkylamino, halogen and $C_1$-$C_4$ haloalkyl and $Z_2$ and $Z_3$ are independently hydrogen or selected from the group represented by $Z_1$; X is chloro or fluoro and n is an integer from 0 to 2; provided that when $R_1$ is methyl, R is not phenyl, phenoxyphenyl or a

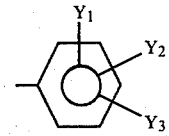

group.

It is preferred that if R is a

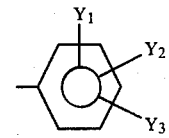

group or $R_1$ is a

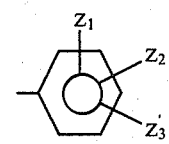

group, that $Y_3$ and $Z_3$ be hydrogen. All remaining unsatisfied valences of the above benzene rings are hydrogen.

The alkyl groups represented by R and $R_1$ include, for example, methyl, ethyl, propyl, isopropyl, butyl, isobutyl, t-butyl, pentyl, hexyl and octyl.

The term "halogen" as used herein includes chlorine, bromine, fluorine and iodine.

The alkoxy groups represented by $R_2$ include, for example, methoxy, ethoxy, propoxy, isopropoxy, butoxy, isobutoxy and the like.

Illustrative of the

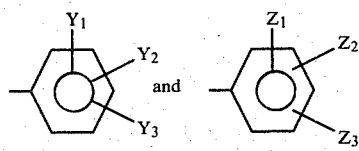

groups which R and $R_1$ represent are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, phenoxyphenyl, methylthiophenyl, butylthiophenyl, dimethylaminophenyl, methylethylaminophenyl, nitrophenyl, and the like and the di- and tri-substituted phenyl groups wherein the substituents are the same or different and are located in the 2, 3, 4, 5 or 6 positions of the phenyl ring, for example, dichlorophenyl, difluorophenyl, methylchlorophenyl, butoxyfluorophenyl, (methyl) (butyl)phenyl, (methoxy) (butoxy)phenyl, dimethoxyphenyl, (nitro) (methyl)phenyl, (methylthio) (ethyl)phenyl, dimethylaminofluorophenyl, (ethylthio) (chloro)phenyl, trichlorophenyl, trimethylphenyl, tributoxyphenyl and the like.

The term "haloalkyl" as employed herein designates alkyl radicals wherein at least one hydrogen atom is replaced by a halogen atom. Groups representative of these radicals include, for example, chloromethyl, iodobutyl, dichloroethyl, dibromopropyl, trichloromethyl, trifluoromethyl and the like.

Groups representative of the cycloalkyl groups represented by $R_1$ include cyclopropyl, cyclobutyl, cyclopentyl, cyclohexyl, cyclooctyl and the like.

In accordance with the present invention, the substituted benzazaphospholes of formula (I) are prepared utilizing the following procedure:

An N-benzylamine of the formula

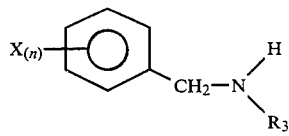
(II)

wherein X and n are above defined and $R_3$ is selected from the group consisting of $C_1$–$C_8$ alkyl, benzyl, trimethylsilyl, phenyl, phenoxyphenyl and a

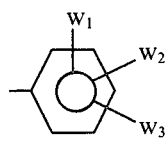

group, wherein $W_1$ is selected from the group consisting of $C_1$–$C_4$ alkyl, $C_1$–$C_4$ alkoxy, $C_1$–$C_4$ haloalkyl, fluoro and chloro and $W_2$ and $W_3$ are independently either hydrogen or selected from the group represented by $W_1$; dissolved in an appropriate solvent is treated with an organolithium compound in the presence of a tertiary diamine within a temperature range of −80° C. to 26° C. to produce a suspension containing a dilithio compound of the formula

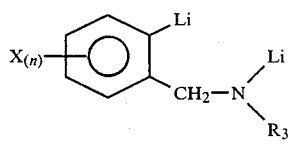
(III)

The dilithio compound of formula (III) is reacted with a substituted phosphonic dichloride of the formula

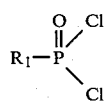
(IV)

wherein $R_1$ is above defined; in an appropriate solvent to yield a substituted benzazaphosphole of the formula

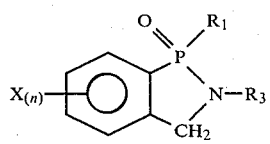
(V)

The reaction of the dilithio compound and the substituted phosphonic dichloride is conducted within a temperature range of −80° C. to 26° C. For ease of reaction and recovery of products, it is preferred to conduct the reaction within a range of from −76° C. to −65° C. When the temperature of the reaction is greater than 26° C., product recovery is difficult due to the presence of various by-products.

In preparing the substituted benzazaphospholes of formula (V), the ratio of reactants is not critical. For each mole of a substituted benzylamine, one should employ two moles of an organolithium compound in order to produce one mole of a dilithio compound of formula (III). Also, one mole of the dilithio compound reacts with one mole of a substituted phosphonic dichloride. It is preferred to employ an excess of the organolithium compound and phosphonic dichloride for ease of reaction and recovery of the reaction product.

Due to the reactive nature of the various reaction intermediates and reactants, the process of the present invention should be conducted in a solvent selected from the class consisting of benzene and liquid alkanes such as cyclohexane, methylcyclohexane, hexane, octane and the like; under essentially anhydrous conditions and in an inert atmosphere.

While the process of this invention can be conducted at atmospheric, sub-atmospheric or super-atmospheric pressure, for convenience and economy it is generally preferred to conduct the process at atmospheric pressure.

Illustrative of the organolithium compounds employed in the processes of this invention include alkyllithiums such as ethyllithium, n-butyllithium, t-butyllithium and aryllithiums such as phenyllithium and the like.

Illustrative of the tertiary diamines employed in the process of the present invention include aliphatic tertiary diamines such as N',N', N',N'-tetramethylethylenediamine and the like and aromatic tertiary such as N,N,N',N'-tetramethyl-o-phenylenediamine; N,N,N',N'-tetramethyl-p-phenylenediamine; bis(N,N-dimethyl-4-aminophenyl)methane and the like.

N-unsubstituted benzazaphospholes of the formula

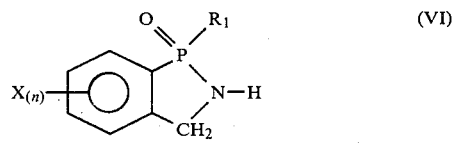
(VI)

are produced by reacting a compound of the formula

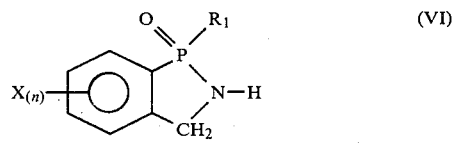
(VII)

with an alcohol at a temperature range of 20° C. to 200° C.

The alcohols utilized in preparing the N-unsubstituted benzazaphospholes should be capable of forming a silyl ether intermediate. Alcohols that may be employed include, for example, methanol, ethanol, propanol, benzyl alcohol and the like. For economy and convenience, methanol is preferred.

N-substituted carbonyl benzazaphosphole derivatives of the formula

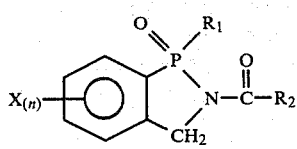

(VIII)

are prepared by reacting the N-unsubstituted benzazaphosphole of formula (VI) with a compound of the formula $$\underset{\text{Cl}-\overset{\overset{\text{O}}{\|}}{\text{C}}-\text{R}_2}{} \quad \text{(IX)}$$

wherein $R_2$ is above defined; in an aprotic solvent within a temperature range of from 20° C. to 200° C.

The following illustrative, non-limiting examples will serve to further demonstrate to those skilled in the art the manner in which specific compounds within the scope of this invention can be prepared. In the examples, all parts are parts by weight unless otherwsie expressly stated.

EXAMPLE 1

Under a static nitrogen atmosphere at 0° C., a solution of n-butyllithium (8.0 g, 0.125 mol) in hexane was added to a solution of tetramethylethylenediamine (14.3 g, 0.123 mol) in 60 ml. of anhydrous cyclohexane with constant stirring. While maintaining the temperature at 0° C., a solution of N-(4-methoxyphenyl)-N-benzylamine (12.8 g, 0.06 mol) in 60 ml. of anhydrous cyclohexane was added to the reaction mixture to produce a suspension containing a dilithio compound. This suspension was stirred for 16 hours at 26° C. and then cooled to −72° C. using a solid carbon dioxide-acetone bath. A solution of isopropylphosphonic dichloride (10.3 g, 0.064 mol) in 60 ml. of anhydrous cyclohexane was rapidly added to the suspension causing the temperature of the reaction to increase to −25° C. The reaction mixture was allowed to cool to −72° C., after which time the solid carbon dioxide-acetone bath was removed and the reaction mixture was stirred for 2 hours. The reaction was quenched with the rapid addition of 12 ml. of acetic acid. The reaction mixture was concentrated under vacuum and the resulting residue was partitioned between methylene chloride and water. The layers were separated and the methylene chloride layer was washed with 5% hydrochloric acid, then with water, dried over magnesium sulfate and concentrated in vacuo to yield a yellow residue. The yellow residue was chromatographically separated on a silica gel column using ethyl acetate as the eluant. Fractions containing the benzazaphosphole were combined and concentrated under vacuum to produce a crude product. The crude product was slurried in ether to yield 1-isopropyl-2-(4-methoxyphenyl)-2,3-dihydro-1H-2,1-benzazaphosphole-1-oxide (3.0 g, 17% yield) as a white solid having a melting point of 135°–137° C. and the following analysis:

Calculated: C, 67.76; H, 6.69; N, 4.65; P, 10.28. Found: C, 67.71; H, 6.69; N, 4.63; P, 10.05.

EXAMPLE 2

The procedure of Example 1 was employed utilizing N-(4-methylphenyl)-N-benzylamine and isopropyl phosphonic dichloride to yield 1-isopropyl-2-(4-methylphenyl)-2,3-dihydro-1H-2,1-benzazaphosphole-1-oxide (5.4 g, 32% yield) as white crystals having a melting point of 135°–137° C. and the following analysis:

Calculated: C, 71.56; H, 7.07; N, 4.91. Found: C, 71.61; H, 7.06; N, 4.89.

EXAMPLE 3

The procedure of Example 1 was employed utilizing N-(4-chlorophenyl)-N-benzylamine and isopropyl phosphonic dichloride to yield 1-isopropyl-2-(4-chlorophenyl)-2,3-dihydro-1H-2,1-benzazaphosphole-1-oxide (2.9 g, 16% yield) as a white solid having a melting point of 172°–174° C. and the following analysis:

Calculated: C, 62.85; H, 5.60; N, 4.58; Cl, 11.60. Found: C, 62.80; H, 5.61; N, 4.67; Cl, 12.08.

EXAMPLE 4

The procedure of Example 1 was employed utilizing N-(3-trifluoromethylphenyl)-N-benzylamine and isopropyl phosphonic dichloride. The crude product produced as a result of the chromatographic separation was crystallized from methylcyclohexane to yield a tan precipitate. The tan precipitate was recrystallized from toluene and petroleum ether to yield 1-isopropyl-2-(3-trifluoromethylphenyl)-2,3-dihydro-1H-2,1-benzazaphosphole-1-oxide as beige plates. A second crop was obtained to give a total yield of 5.9 g, (29% yield) of 1-isopropyl-2-(3-trifluoromethylphenyl)-2,3-dihydro-1H-2,1-benzazaphosphole-1-oxide having a melting point of 117°–119° C. and the following analysis:

Calculated: C, 60.18; H, 5.05; N, 4.13; F, 16.80; P, 9.13. Found: C, 60.12; H, 5.07; N, 4.12; F, 16.56; P, 9.23.

EXAMPLE 5

The procedure of Example 1 was employed utilizing N-(3-methylphenyl)-N-benzylamine and isopropyl phosphonic dichloride. The crude product produced as a result of the chromatographic separation was distilled at 150° C. and 0.8 mm to yield a pale yellow glass. The yellow glass was crystallized from methylcyclohexane to yield 1-isopropyl-2-(3-methylphenyl)-2,3-dihydro-1H-2,1-benzazaphosphole-1-oxide (3.5 g, 20% yield) as a white crystalline solid having a melting point of 112°–113° C. and the following analysis:

Calculated: C, 71.56; H, 7.07; N, 4.91. Found: C, 71.57; H, 7.05; N, 4.83.

EXAMPLE 6

The procedure of Example 1 was employed utilizing N-benzylaniline and methyl phosphonic dichloride. The crude product produced as a result of the chromatographic separation yielded without additional purification 1-methyl-2-phenyl-2,3-dihydro-1H-2,1-benzazaphosphole-1-oxide (0.4 g, 1.75% yield) as a brown glass.

EXAMPLE 7

The procedure of Example 1 was employed utilizing N-benzylaniline and cyclohexyl phosphonic dichloride. The crude product produced as a result of the chromatographic separation yielded without additional purification 1-cyclohexyl-2-phenyl-2,3-dihydro-1H-2,1-benzazaphosphole-1-oxide (2.7 g, 14.5% yield) as a beige solid having a melting point of 167°–169° C. and the following analysis:

Calculated: C, 73.29; H, 7.12; N, 4.50. Found: C, 73.19; H, 7.11; N, 4.48.

EXAMPLE 8

The procedure of Example 1 was employed utilizing N-benzylaniline and cyclopentyl phosphonic dichloride. The crude product produced as a result of the chromatographic separation was slurried in methylcyclohexane and further purified on a chromatographic system employing an alumina column using chloroform (containing 0.75% ethyl alcohol) as the eluant. Fractions containing the benzazaphosphole were crystallized using benzene and methylcyclohexane to yield 1-cyclopentyl-2-phenyl-2,3-dihydro-1H-2,1-benzazaphosphole-1-oxide as a yellow solid. A second crop was obtained to give a total yield of 0.85 g (5% yield) of 1-cyclopentyl-2-phenyl-2,3-dihydro-1H-2,1-benzazaphosphole-1-oxide having a melting point of 123°–125° C. and the following analysis:

Calculated: C, 72.71; H, 6.78; N, 4.71; P, 10.42. Found: C, 72.81; H, 6.81; N, 4.67; P, 10.26.

EXAMPLE 9

The procedure of Example 1 was employed utilizing N-benzylaniline and 2,4-dimethoxyphenyl phosphonic dichloride. The reaction of the dilithio compound and the 2,4-dimethoxyphenyl phosphonic dichloride was conducted at −76° C. to yield 1-(2,4-dimethoxyphenyl)-2-phenyl-2,3-dihydro-1H-2,1-benzazaphosphole-1-oxide (7.2 g, 66% yield) as a white solid having a melting point of 173°–175° C. and the following analysis:

Calculated: C, 69.03; H, 5.52; N, 3.83. Found: C, 68.99; H, 5.52; N, 3.79.

EXAMPLE 10

The procedure of Example 1 was employed utilizing N-benzylaniline and ethyl phosphonic dichloride. The reaction of the dilithio compound and the ethyl phosphonic dichloride was conducted at −76° C. to yield 1-ethyl-2-phenyl-2,3-dihydro-1H-2,1-benzazaphosphole-1-oxide (0.45 g, 6% yield) as a pale yellow solid having a melting point of 116°–120° C. and the following analysis:

Calculated: C, 70.03; H, 6.27; N, 5.44. Found: C, 70.04; H, 6.27; N, 5.39.

EXAMPLE 11

The procedure of Example 1 was employed utilizing N-benzylaniline and 4-methylthiophenyl phosphonic dichloride. The reaction of the dilithio compound and the 4-methylthiophenyl phosphonic dichloride was conducted at −76° C. to yield a beige solid. The beige solid was recrystallized from ethyl acetate to yield 1-(4-methylthiophenyl)-2-phenyl-2,3-dihydro-1H-2,1-benzazaphosphole-1-oxide (2.1 g, 11% yield) as a white solid having a melting point of 164°–167° C. and the following analysis:

Calculated: C, 68.36; H, 5.16; N, 3.99. Found: C, 68.41; H, 5.16; N, 3.98.

EXAMPLE 12

The procedure of Example 1 was employed utilizing N-3-methylphenyl-N-benzylamine and phenyl phosphonic dichloride. The reaction of the dilithio compound and the phenyl phosphonic dichloride was conducted at 0° C. The crude product produced as a result of the chromatographic separation was crystallized from diethyl ether then recrystallized from carbon tetrachloride to yield 1-phenyl-2-(3-methylphenyl)-2,3-dihydro-1H-2,1-benzazaphosphole-1-oxide as a yellow solid. A second crop was obtained to give a total yield of 1.2 g (12% yield) of 1-phenyl-2-(3-methylphenyl)-2,3-dihydro-1H-2,1-benzazaphosphole-1-oxide having a melting point of 190°–192° C. and the following analysis:

Calculated: C, 75.22; H, 5.68; N, 4.39. Found: C, 74.44; H, 5.88; N, 4.49.

EXAMPLE 13

The procedure of Example 1 was employed utilizing N-benzylaniline and isopropyl phosphonic dichloride. The reaction of the dilithio compound and the isopropyl phosphonic dichloride was conducted at −65° C. to yield 1-isopropyl-2-phenyl-2,3-dihydro-1H-2,1-benzazaphosphole-1-oxide (1.8 g, 11% yield) as a white solid having a melting point of 145°–147° C. and the following analysis:

Calculated: C, 70.84; H, 6.69; N, 5.16. Found: C, 70.80; H, 6.72; N, 5.15.

EXAMPLE 14

The procedure of Example 1 was employed utilizing N-benzylaniline and octyl phosphonic dichloride. The reaction of the dilithio compound and the octyl phosphonic dichloride was conducted at −65° C. The crude product produced as a result of the chromatographic separation was dissolved in methylene chloride and separated on a Woelm's neutral alumina column using ethyl acetate as the eluant to yield 1-octyl-2-phenyl-2,3-dihydro-1H-2,1-benzazaphosphole-1-oxide (1.1 g, 5% yield) as a pale yellow oil ($n_D$=1.5502).

EXAMPLE 15

The procedure of Example 1 was employed utilizing dibenzylamine and isopropyl phosphonic dichloride. The reaction of the dilithio compound and the isopropyl phosphonic dichloride was conducted at −65° C. The crude product produced as a result of the chromatographic separation was distilled at 160° C. and 0.2 mm to yield a colorless oil. The colorless oil was slurried in petroleum ether to yield 1-isopropyl-2-phenylmethyl-2,3-dihydro-1H-2,1-benzazaphosphole-1-oxide (1.15 g, 12% yield) as a colorless solid having a melting point of 145°–147° C. and the following analysis:

Calculated: C, 71.56; H, 7.07; N, 4.91. Found: C, 71.47; H, 7.05; N, 4.84.

EXAMPLE 16

The procedure of Example 1 was employed utilizing N-benzylaniline and 3-methoxyphenyl phosphonic dichloride. The reaction of the dilithio compound and the 3-methoxyphenyl phosphonic dichloride was conducted at 0° C. to yield 1-(3-methoxyphenyl)-2-phenyl-2,3-dihydro-1H-2,1-benzazaphosphole-1-oxide (2.75 g, 27% yield) as a solid having a melting point of 170°–172° C. and the following analysis:

Calculated: C, 71.63; H, 5.41; N, 4.18. Found: C, 71.65; H, 5.38; N, 4.17.

EXAMPLE 17

The procedure of Example 1 was employed utilizing N-benzylaniline and 2-methylphenyl phosphonic dichloride. The reaction of the dilithio compound and the 2-methylphenyl phosphonic dichloride was conducted at 0° C. to yield 1-(2-methylphenyl)-2-phenyl-2,3-dihydro-1H-2,1-benzazaphosphole-1-oxide (0.8 g, 8% yield)

as a yellow solid having a melting point of 181°–183° C. and the following analysis:

Calculated: C, 75.22; H, 5.68; N, 4.39. Found: C, 74.11; H, 5.59; N, 4.29.

EXAMPLE 18

The procedure of Example 1 was employed utilizing N-benzylaniline and 4-dimethylaminophenyl phosphonic dichloride. The reaction of the dilithio compound and the 4-dimethylaminophenyl phosphonic dichloride was conducted at 0° C. The crude product produced as a result of the chromatographic separation was crystallized from ethyl acetate to yield 1-[(4-dimethylamino)phenyl]-2-phenyl-2,3-dihydro-1H-2,1-benzazaphosphole-1-oxide (4.1 g, 44% yield) as a white solid having a melting point of 228°–229° C. and the following analysis:

Calculated: C, 72.40; H, 6.08; N, 8.04. Found: C, 72.51; H, 6.11; N, 8.02.

EXAMPLE 19

The procedure of Example 1 was employed utilizing N-benzylaniline and 3,4-dimethoxyphenyl phosphonic dichloride. The reaction of the dilithio compound and the 3,4-dimethoxyphenyl phosphonic dichloride was conducted at 0° C. The crude product produced as a result of the chromatographic separation was dissolved in ethyl acetate and crystallized from diethyl ether to yield 1-(3,4-dimethoxyphenyl)-2-phenyl-2,3-dihydro-1H-2,1-benzazaphosphole-1-oxide (3.7 g, 34% yield) as beige plates having a melting point of 84°–86° C. and the following analysis:

Calculated: C, 69.03; H, 5.52; N, 3.83. Found: C, 68.83; H, 5.72; N, 3.80.

EXAMPLE 20

The procedure of Example 1 was employed utilizing N-benzylaniline and 4-phenoxyphenyl phosphonic dichloride. The reaction of the dilithio compound and the 4-phenoxyphenyl phosphonic dichloride was conducted at 0° C. The crude product produced as a result of the chromatographic separation was distilled at 140° C. and the resulting residue was crystallilzed from diethyl ether to yield 1-(4-phenoxyphenyl)-2-phenyl-2,3-dihydro-1H-2,1-benzazaphosphole-1-oxide as beige needles. A second crop was obtained to give a total yield of 0.75 g, 3% yield of 1-(4-phenoxyphenyl)-2-phenyl-2,3-dihydro-1H-2,1-benzazaphosphole-1-oxide having a melting point of 207°–208° C. and the following analysis:

Calculated: C, 75.56; H, 5.07; N, 3.52. Found: C, 75.48; H, 5.07; N, 3.48.

EXAMPLE 21

The procedure of Example 1 was employed utilizing N-t-butyl-N-benzylamine and phenyl phosphonic dichloride. The reaction of the dilithio compound and the phenyl phosphonic dichloride was conducted at 0° C. The crude product produced as a result of the chromatographic separation was distilled at 160° C. and 0.2 mm to yield a colorless oil. The colorless oil was slurried in petroleum ether to yield 1-phenyl-2-(t-butyl)-2,3-dihydro-1H-2,1-benzazaphosphole-1-oxide (2.75 g, 16% yield) as a white solid having a melting point of 89°–91° C. and the following analysis:

Calculated: C, 71.56; H, 7.07; N, 4.91. Found: C, 71.48; H, 7.02; N, 4.85.

EXAMPLE 22

Under a static nitrogen atmosphere at 0° C., a solution of n-butyllithium (7.87 g, 0.123 mol) in hexane was added to a solution of tetramethylethylenediamine (14.3 g, 0.123 mol) in 60 ml. of anhydrous cyclohexane with constant stirring. The resulting mixture was stirred for an additional 15 minutes and then cooled to −70° C. using a solid carbon dioxide-acetate bath. A solution of N-methyl-4-chloro-benzylamine (9.6 g, 0.06 mol) in 60 ml. of anhydrous cyclohexane was added to the reaction mixture to produce a suspension containing a dilithio compound. This suspension was stirred for 2 hours at 26° C. and then cooled to −70° C. using a solid carbon dioxide-acetone bath. A solution of phenylphosphonic dichloride (12.5 g, 0.064 mol) in 60 ml. of anhydrous cyclohexane was rapidly added to the suspension causing the temperature of the reaction to increase to −20° C. The reaction mixture was allowed to cool to −70° C., after which time the solid carbon dioxide-acetone bath was removed and the reaction mixture was stirred for 2.5 hours. The reaction mixture was cooled to 0° C. and then quenched with the rapid addition of 12 ml. of acetic acid. The cyclohexane was removed on a rotary evaporator, and the resulting residue was partitioned between methylene chloride and water. The layers were separated and the methylene chloride layer was dried over magnesium sulfate and concentrated in vacuo to yield a red oil. Distillation of the red oil at 180° C. and 0.25 mm yielded a yellow solid which was slurried in ether to yield 1-phenyl-2-methyl-6-chloro-2,3-dihydro-1H-2,1-benzazaphosphole-1-oxide (2.2 g, 13% yield) as a pale yellow solid having a melting point of 159°–162° C. and the following analysis:

Calculated: C, 60.55; H, 4.72; N, 5.04. Found: C, 60.59; H, 4.72; N, 5.06.

EXAMPLE 23

Under a static nitrogen atmosphere at 0° C., a solution of n-butyllithium (8 g, 0.125 mol) in hexane was added to a solution of tetramethylethylenediamine (14.3 g, 0.123 mol) in 60 ml. of anhydrous cyclohexane with constant stirring. While maintaining the temperature of the reaction at 0° C., a solution of N-trimethylsilylbenzylamine (10.75 g, 0.06 mol) in 60 ml. of anhydrous cyclohexane was added to the reaction mixture to produce a suspension containing a dilithio compound. This suspension was stirred for 16.5 hours at 26° C. and then cooled to −72° C. using a solid carbon dioxide-acetone bath. A solution of isopropylphosphonic dichloride (10.3 g, 0.064 mol) in 60 ml. of anhydrous cyclohexane was rapidly added to the suspension causing the temperature of the reaction to increase to −10° C. The reaction mixture was allowed to cool to −72° C., after which time the solid carbon dioxide-acetone bath was removed and the reaction mixture was stirred for 1.5 hours at 26° C. The reaction mixture was cooled to 0° C. and then quenched with the rapid addition of 12 ml. of acetic acid. The reaction mixture was concentrated under vacuum and the resulting residue was partitioned between methylene chloride and water. The layers were separated and the methylene chloride layer was dried over magnesium sulfate and concentrated in vacuo to yield a red oil. The red oil was distilled at 180° C. and 0.2 mm to yield 1-isopropyl-2-trimethylsilyl-2,3-dihydro-1H-2,1-benzazaphosphole-1-oxide.

The 1-isopropyl-2-trimethylsilyl-2,3-dihydro-1H-2,1-benzazaphosphole-1-oxide was added to 50 ml. of methanol and allowed to stand for 40 hours. The methanol was removed under vacuum and the resulting residue was slurried in ether to yield 1-isopropyl-2,3-dihydro-1H-2,1-benzazaphosphole-1-oxide as a white solid. A second crop was obtained to give a total yield of 2.35 g (20% yield) of 1-isopropyl-2,3-dihydro-1H-2,1-benzazaphosphole-1-oxide having a melting point of 149°–151° C. and the following analysis:

Calculated: C, 61.53; H, 7.23; N, 7.18; P, 15.87. Found: C, 61.43; H, 7.25; N, 7.10; P, 15.75.

EXAMPLE 24

Under a static nitrogen atmosphere at 0° C., a solution of n-butyllithium (16 g, 0.25 mol) in hexane was added to a solution of tetramethylethylenediamine (28.6 g, 0.246 mol) in 120 ml. of anhydrous cyclohexane with constant stirring. While maintaining the temperature of the reaction at 0° C., a solution of N-trimethylsilylbenzylamine (21.6 g, 0.12 mol) in 60 ml. of anhydrous cyclohexane was added to the reaction mixture to produce a suspension containing a dilithio compound. This suspension was stirred for 16 hours at 26° C. and then cooled to $-76°$ C. using a solid carbon dioxide-acetone bath. A solution of phenylphosphonic dichloride (25 g, 0.128 mol) in 120 ml. of anhydrous cyclohexane was rapidly added to the suspension causing the temperature of the reaction to increase to $-15°$ C. The reaction mixture was allowed to cool to $-76°$ C., after which time the solid carbon dioxide-acetone bath was removed and the reaction mixture was stirred for 3 hours. The reaction mixture was cooled to 0° C., then quenched with the rapid addition of 24 ml. of acetic acid. After stirring the reaction mixture for 5 minutes, the cyclohexane was removed on a rotary evaporator, and the resulting residue was partitioned between methylene chloride and water. The layers were separated and the methylene chloride layer was dried over magnesium sulfate and concentrated in vacuo to yield an oil. Distillation of this oil at 180° C. and 0.3 mm yielded 1-phenyl-2-trimethylsilyl-2,3-dihydro-1H-2,1-benzazaphosphole-1-oxide.

The 1-phenyl-2-trimethylsilyl-2,3-dihydro-1H-2,1-benzazaphosphole-1-oxide was dissolved in 50 ml. of methanol and heated at reflux for 4 hours. After stirring for 16 hours at 26° C., the resulting solution was concentrated in vacuo and the residue was crystallized from ethyl acetate to yield 1-phenyl-2,3-dihydro-1H-2,1-benzazaphosphole-1-oxide (9.0 g, 33% yield) as a white solid having a melting point of 177°–180° C. and the following analysis:

Calculated: C, 68.12; H, 5.28; N, 6.11. Found: C, 67.83; H, 5.23; N, 6.03.

EXAMPLE 25

Under a static nitrogen atmosphere at 0° C., a solution of n-butyllithium (3.9 g, 0.061 mol) in hexane was added to a solution of tetramethylethylenediamine (1.8 g, 0.0155 mol) in 30 ml. of anhydrous cyclohexane with constant stirring. While maintaining the temperature of the reaction at 0° C., a solution of N-benzyl-4-toluidine (5.9 g, 0.03 mol) in 30 ml. of anhydrous cyclohexane was added to the reaction mixture to produce a suspension containing a dilithio compound. The suspension containing the dilithio compound was stirred for 4 hours at 26° C. and then cooled to 0° C. A solution of phenylphosphonic dichloride (6.25 g, 0.032 mol) in 30 ml. of anhydrous cyclohexane was added dropwise to the suspension and the resulting mixture was stirred for 1.5 hours at 26° C. The reaction was quenched with the rapid addition of 6 ml. of acetic acid. The mixture was concentrated in vacuo and the resulting residue partitioned in methylene chloride and water. The layers were separated and the methylene chloride layer was washed with 5% hydrochloric acid, then water, dried over sodium sulfate and concentrated in vacuo to yield a brown-green glass. The brown-green glass was crystallized from ethyl acetate to yield light green plates which were recrystallized from toluene to yield 1-phenyl-2-(4-methylphenyl)-2,3-dihydro-1H-2,1-benzazaphosphole-1-oxide (1.9 g, 20% yield) as white crystals having a melting point of 197°–199° C. and the following analysis:

Calculated: C, 75.22; H, 5.68; N, 4.39. Found: C, 75.62; H, 5.61; N, 4.33

EXAMPLE 26

Under a static nitrogen atmosphere at 0° C., a solution of n-butyllithium (4.03 g, 0.063 mol) in hexane was added to a solution of tetramethylethylenediamine (1.86 g, 0.016 mol) in 30 ml. of anhydrous cyclohexane with constant stirring. While maintaining the temperature of the reaction at 0° C., a solution of N-benzylaniline (5.5 g, 0.03 mol) in 30 ml. of anhydrous cyclohexane was added to the reaction mixture to produce a suspension containing a dilithio compound. The suspension was stirred for 2 hours at 26° C. and then cooled to 0° C. A solution of 4-chlorophenylphosphonic dichloride (7.35 g, 0.032 mol) in 30 ml. of anhydrous cyclohexane was rapidly added to the suspension. After stirring for 15 minutes at 0° C., the resulting mixture was stirred for 2 hours at 26° C. The reaction mixture was cooled to 0° C., then quenched with the rapid addition of 6 ml. of acetic acid. After stirring for 15 minutes, the cyclohexane was removed on a rotary evaporator and the resulting residue was partitioned between methylene chloride and water. The layers were separated and the methylene chloride layer was washed with 5% hydrochloric acid, then water, dried with sodium sulfate and concentrated in vacuo to yield a blue oil. The blue oil was separated on a silica gel column using first methylene chloride then a 3:1 mixture of methylene chloride:ethyl acetate as the eluant. Fractions containing the benzazaphosphole were combined and concentrated in vacuo to yield a crude product. The crude product was slurried in anhydrous diethyl ether to yield 1-(4-chlorophenyl)-2-phenyl-2,3-dihydro-1H-2,1-benzazaphosphole-1-oxide (1.0 g, 5% yield) as a white crystalline solid having a melting point of 180°–182° C. and the following analysis:

Calculated: C, 67.17; H, 4.45; N, 4.12; Cl, 10.43. Found: C, 67.05; H, 4.51; N, 4.09; Cl, 10.36.

EXAMPLE 27

The procedure of Example 26 was employed utilizing N-benzylaniline and 4-methylphenyl phosphonic dichloride to yield 1-(4-methylphenyl)-2-phenyl-2,3-dihydro-1H-2,1-benzazaphosphole-1-oxide (0.65 g, 7% yield) as a white solid having a melting point of 180°–181° C. and the following analysis:

Calculated: C, 75.22; H, 5.68; N, 4.39. Found: C, 75.23; H, 5.66; N, 4.36.

EXAMPLE 28

The procedure of Example 26 was employed utilizing N-benzylaniline and 4-fluorophenyl phosphonic dichloride to yield a pale yellow solid. The yellow solid was recrystallized from ethyl acetate to yield 1-(4-fluorophenyl)-2-phenyl-2,3-dihydro-1H-2,1-benzazaphosphole-1-oxide (5.9 g, 30% yield) as white needles having a melting point of 119°–120° C. and the following analysis:

Calculated: C, 70.59; H, 4.68; N, 4.33. Found: C, 70.48; H, 4.69; N, 4.32.

EXAMPLE 29

The procedure of Example 26 was employed utilizing N-benzylaniline and 4-methoxyphenyl phosphonic dichloride to yield 1-(4-methoxyphenyl)-2-phenyl-2,3-dihydro-1H-2,1-benzazaphosphole-1-oxide (0.7 g, 7% yield) as a white solid having a melting point of 190°–192° C. and the following analysis:

Calculated: C, 71.63; H, 5.41; N, 4.18. Found: C, 71.61; H, 5.39; N, 4.18.

EXAMPLE 30

Under a static nitrogen atmosphere at 0° C., a solution of n-butyllithium (8.0 g, 0.125 mol) in hexane was added to a solution of tetramethylethylenediamine (14.3 g, 0.123 mol) in 60 ml. of anhydrous cyclohexane with constant stirring. While maintaining the temperature at 0° C., a solution of dibenzylamine (11.8 g, 0.06 mol) in 30 ml. of anhydrous cyclohexane was added to the reaction mixture to produce a suspension containing a dilithio compound. This suspension was stirred for 2 hours at 26° C. and then cooled to −76° C. using a solid carbon dioxide-acetone bath. A solution of phenylphosphonic dichloride (12.5 g, 0.064 mol) in 30 ml. of anhydrous cyclohexane was rapidly added to the suspension causing the temperature of the reaction to increase to 0° C. The reaction mixture was allowed to cool to −76° C., after which time the reaction mixture was stirred for 0.25 hours. The solid carbon dioxide-acetone bath was then removed and the reaction mixture was stirred for an additional 2 hours at 26° C. The reaction mixture was cooled to 0° C. and then quenched with the rapid addition of 12 ml. of acetic acid. The cyclohexane was removed on a rotary evaporator, and the resulting residue partitioned between methylene chloride and water. The layers were separated and the methylene chloride layer was dried and concentrated in vacuo to yield an orange glass. The orange glass was distilled at 220° C. and 0.25 torr and the resulting solid residue was chromatographically separated on a silica gel column using ethyl acetate as the eluant. Fractions containing the benzazaphosphole were combined and concentrated in vacuo to produce a crude product. The crude product was crystallized from diethyl ether and petroleum ether to yield 1-phenyl-2-(phenylmethyl)-2,3-dihydro-1H-2,1-benzazaphosphole-1-oxide (6.15 g, 32% yield) as a white solid having a melting point of 99°–101° C. and the following analysis:

Calculated: C, 75.22; H, 5.68; N, 4.39. Found: C, 75.15; H, 5.69; N, 4.31.

EXAMPLE 31

The procedure of Example 30 was employed utilizing N-methyl-N-benzylamine and isopropyl phosphonic dichloride. The reaction of the dilithio compound and the isopropyl phosphonic dichloride was conducted at −72° C. The crude product produced as a result of the chromatographic separation was slurried in methylcyclohexane to yield a pale solid. The solid was recrystallized from diethyl ether and petroleum ether to yield 1-isopropyl-2-methyl-2,3-dihydro-1H-2,1-benzazaphosphole-1-oxide as a crystalline precipitate. A second crop was obtained to give a total yield of 2.35 g (19% yield) of 1-isopropyl-2-methyl-2,3-dihydro-1H-2,1-benzazaphosphole-1-oxide having a melting point of 72°–74° C. and the following analysis:

Calculated: C, 63.15; H, 7.71; N, 6.69. Found: C, 63.12; H, 7.69; N, 6.61.

EXAMPLE 32

The procedure of Example 30 was employed utilizing N-t-butyl-N-benzylamine and isopropyl phosphonic dichloride. The reaction of the dilithio compound and the isopropyl phosphonic dichloride was conducted at −70° C. The crude product produced as a result of the chromatographic separation was distilled at 130° C. and 0.1 mm to yield a colorless oil. The colorless oil was slurried in petroleum ether to yield 1-isopropyl-2-t-butyl-2,3-dihydro-1H-2,1-benzazaphosphole-1-oxide (5.8 g, 39% yield) having a melting point of 67°–70° C. and the following analysis:

Calculated: C, 66.91; H, 8.82; N, 5.57. Found: C, 65.15; H, 8.87; N, 5.39.

EXAMPLE 33

The procedure of Example 30 was employed utilizing N-isopropyl-N-benzylamine and isopropyl phosphonic dichloride. The reaction of the dilithio compound and the isopropyl phosphonic dichloride was conducted at −70° C. The crude product produced as a result of the chromatographic separation was distilled at 130° C. and 0.1 mm to yield a colorless oil. This oil was slurried in petroleum ether to yield 1,2-diisopropyl-2,3-dihydro-1H-2,1-benzazaphosphole-1-oxide (2.28 g, 16% yield) as a pale yellow oil having the following analysis:

Calculated: C, 65.80; H, 8.50; N, 5.90. Found: C, 62.25; H, 8.39; N, 5.70.

EXAMPLE 34

Under a static nitrogen atmosphere at 0° C., a solution of n-butyllithium (8 g, 0.125 mol) in hexane was added to a solution of tetramethylethylenediamine (14.3 g, 0.123 mol) in 30 ml. of anhydrous cyclohexane with constant stirring. While maintaining the temperature at 0° C., a solution of N-ethylbenzylamine (8.1 g, 0.06 mol) in 60 ml. of anhydrous cyclohexane was added to the reaction mixture to produce a suspension containing a dilithio compound. This suspension was stirred for 3 hours at 26° C. and then cooled to −71° C. using a solid carbon dioxide-acetone bath. A solution of phenylphosphonic dichloride (12.5 g, 0.064 mol) in 30 ml. of anhydrous cyclohexane was rapidly added to the suspension causing the temperature of the reaction to increase to −20° C. When the reaction temperature began to decrease, the solid carbon dioxide-acetone bath was removed and the reaction mixture was stirred for 2 hours. The reaction mixture was cooled to 0° C. and then quenched with the rapid addition of 12 ml. of acetic acid. After stirring for 10 minutes, the cyclohexane was removed on a rotary evaporator, and the resulting residue was partitioned between methylene chloride and water. The layers were separated and the methylene chloride layer was washed with brine, dried over magnesium sulfate and concentrated in vacuo to yield an orange oil. This oil was distilled at 170° C. and 0.2 torr, yielding a yellow oil which was then slurried in diethyl ether to yield a white solid. The white solid was purified on a silica gel column using ethyl acetate as the eluant. Fractions containing the benzazaphosphole were combined and concentrated in vacuo to produce a crude product. The crude product was slurried in ether to yield 1-phenyl-2-ethyl-2,3-dihydro-1H-2,1-benzazaphosphole-1-oxide as a crystalline precipitate. A second crop was obtained from the ether filtrate and the combined product yield was recrystallized from methylcyclohexane to yield 1-phenyl-2-ethyl-2,3-dihydro-1H-2,1-benzazaphosphole-1-oxide (1.3 g, 8% yield) as white crystals having a melting point of 94°–95° C. and the following analysis:

Calculated: C, 70.03; H, 6.27; N, 5.44. Found: C, 70.04; H, 6.27; N, 5.39.

EXAMPLE 35

Under a static nitrogen atmosphere at 26° C., a solution of n-butyllithium (3.93 g, 7.13 mol) in hexane was added to a solution of tetramethylethylenediamine (1.8 g, 0.0155 mol) in 30 ml. of anhydrous cyclohexane with constant stirring. The reaction mixture was cooled to 0° C. and then a solution of N-benzylaniline (5.5 g, 0.03 mol) in 30 ml. of anhydrous cyclohexane was added to the mixture to produce a suspension containing a dilithio compound. This suspension was stirred for 2.5 hours at 26° C. and then cooled to 0° C. A solution of t-butylphosphonic dichloride (5.6 g, 0.032 mol) in 30 ml. of anhydrous cyclohexane was added dropwise to the suspension and the resulting mixture was stirred for 1.5 hours at 26° C. The reaction mixture was cooled to 0° C. and then quenched with the rapid addition of 10 ml. of a saturated solution of ammonium chloride. The resulting mixture was concentrated in vacuo and the residue was partitioned in methylene chloride and water. The layers were separated and the methylene chloride layer was washed with 5% hydrochloric acid, then with water, dried over sodium sulfate and concentrated in vacuo to yield a red oil. The red oil was separated on a silica gel column using ethyl acetate as the eluant. Fractions containing the benzazaphosphole were combined and concentrated in vacuo to produce a crude product. The crude product was triturated with isopropyl ether and petroleum ether to yield a white solid. The white solid was recrystallized from isopropyl ether to yield 1-(t-butyl)-2-pheny-2,3-dihydro-1H-2,1-benzazaphosphole-1-oxide (0.7 g, 8% yield) as colorless needles having a melting point of 171°–172° C. and the following analysis:

Calculated: C, 71.56; H, 7.07; N, 4.91. Found: C, 71.61; H, 7.07; N, 4.79.

EXAMPLE 36

Under a static nitrogen atmosphere at 0° C., a solution of n-butyllithium (7.87 g, 0.123 mol) in hexane was added to a solution of tetramethylethylenediamine (14.3 g, 0.123 mol) in 60 ml. of anhydrous cyclohexane with constant stirring. While maintaining the temperature of the reaction at 0° C., a solution of N-isopropylbenzylamine (9 g, 0.06 mol) in 60 ml. of anhydrous cyclohexane was added to the reaction mixture to produce a suspension containing a dilithio compound. This suspension was stirred for 2 hours at 26° C. and then cooled to −40° C. using a solid carbon dioxide-acetone bath. A solution of phenylphosphonic dichloride (12.5 g, 0.064 mol) in 60 ml. of anhydrous cyclohexane was rapidly added to the suspension causing the temperature of the reaction to increase to 10° C. The reaction mixture was stirred for 1.5 hours at 26° C., after which time the reaction mixture was cooled to 0° C. and then quenched with the rapid addition of 12 ml. of acetic acid. After stirring for 15 minutes, the cyclohexane was removed on a rotary evaporator, and the resulting residue was partitioned between methylene chloride and water. The layers were separated and the methylene chloride layer was washed with water, dried over magnesium sulfate and concentrated in vacuo to yield an oil. This oil was distilled at 160° C. and 0.2 torr and the resulting residue was crystallized at 0° C. from diethyl ether and petroleum ether to yield 2-(1-isopropyl)-1-phenyl-2,3-dihydro-1H-2,1-benzazaphosphole-1-oxide (4.5 g, 28% yield) having a melting point of 92°–94° C. and the following analysis:

Calculated: C, 70.84; H, 6.69; N, 5.16. Found: C, 70.80; H, 6.72; N, 5.15.

EXAMPLE 37

The procedure of Example 36 was employed utilizing N-methyl-N-benzylamine and phenyl phosphonic dichloride. The reaction of the dilithio compound and the phenyl phosphonic dichloride was conducted at −60° C. The residue produced as a result of the distillation process was slurried in ether to yield 1-phenyl-2-methyl-2,3-dihydro-1H-2,1-benzazaphosphole-1-oxide as a white solid. A second crop was obtained and the combined product yield was recrystallized from carbon tetrachloride and petroleum ether to yield 1-phenyl-2-methyl-2,3-dihydro-1H-2,1-benzazaphosphole-1-oxide (2.25 g, 15% yield) having a melting point of 129°–130° C. and the following analysis:

Calculated: C, 69.13; H, 5.80; N, 5.76. Found: C, 68.69; H, 5.77; N, 572.

EXAMPLE 38

Under a static nitrogen atmosphere at 0° C., a solution of n-butyllithium (3.93 g, 0.0615 mol) in hexane was added to a solution of tetramethylethylenediamine (7.13 g, 0.0615 mol) in 30 ml. of anhydrous cyclohexane with constant stirring. While maintaining the temperature of the reaction at 0° C., a solution of N-benzylaniline (5.5 g, 0.03 mol) in 30 ml. of anhydrous cyclohexane was added to the reaction mixture to produce a suspension containing a dilithio compound. This suspension was stirred for 2 hours at 26° C. and then cooled to 0° C. A solution of 2-anisylphosphonic dichloride (7.2 g, 0.032 mol) in 30 ml. of benzene was rapidly added to the suspension. The resulting mixture was stirred for 0.75 hours at 0° C., then stirred at 26° C. for 2 hours. The reaction mixture was then cooled to 0° C., and quenched with the rapid addition of 6 ml. of acetic acid. After stirring for 15 minutes, the reaction mixture was concentrated under vacuum and the resulting residue was partitioned in methylene chloride and water. The layers were separated and the methylene chloride layer was washed with 5% hydrochloric acid, then water, dried with sodium sulfate and concentrated in vacuo to yield a brown residue. The brown residue was chromatographically separated on a silica gel column using a 3:1 mixture of methylene chloride:ethyl acetate as the eluant. Fractions containing the benzazaphosphole were combined and concentrated in vacuo to produce a crude product. The crude product was triturated with diethyl ether to yield 1-(2-methoxyphenyl)-2-phenyl-2,3-dihydro-1H-2,1-benzazaphosphole-1-oxide (2.05 g, 20% yield) as a white solid having a melting point of 189°–191° C. and the following analysis:

Calculated: C, 71.63; H, 5.41; N, 4.18. Found: C, 71.49; H, 5.72; N, 4.08.

EXAMPLE 39

The procedure of Example 38 was employed utilizing N-benzylaniline and 3-fluorophenyl phosphonic dichloride to yield 1-(3-fluorophenyl)-2-phenyl-2,3-dihydro-1H-2,1-benzazaphosphole-1-oxide (1.3 g, 13% yield) as a white solid having a melting point of 209°–210° C. and the following analysis:

Calculated: C, 70.59; H, 4.68; N, 4.33. Found: C, 70.55; H, 4.66; N, 4.31.

EXAMPLE 40

The procedure of Example 38 was employed utilizing N-benzylaniline and 3-methylphenyl phosphonic dichloride to yield 1-(3-methylphenyl)-2-phenyl-2,3-dihydro-1H-2,1-benzazaphosphole-1-oxide (2.5 g, 26% yield) as a white solid having a melting point of 155°–156° C., and the following analysis:

Calculated: C, 75.22; H, 5.68; N, 4.39. Found: C, 75.28; H, 5.67; N, 4.36.

EXAMPLE 41

The procedure of Example 38 was employed utilizing N-benzylaniline and 4-trifluoromethylphenyl phosphonic dichloride. The crude product produced as a result of the chromatographic separation was crystallized from diethyl ether and petroleum ether and recrystallized from diethyl ether to yield 1-[4-(trifluoromethyl)phenyl]-2-phenyl-2,3-dihydro-1H-2,1-benzazaphosphole-1-oxide (0.5 g, 4% yield) having a melting point of 187°–189° C.

EXAMPLE 42

Under a static nitrogen atmosphere at 0° C., a solution of n-butyllithium (3.90 g, 0.061 mol) in hexane was added to a solution of tetramethylethylenediamine (1.8 g, 0.0155 mol) in 30 ml. of anhydrous cyclohexane with constant stirring. While maintaining the temperature of the reaction at 0° C., a solution of N-benzylaniline (5.5 g, 0.03 mol) in 30 ml. of anhydrous cyclohexane was added to the reaction mixture to produce a suspension containing a dilithio compound. This suspension was stirred for 2 hours at 26° C. and then cooled to 0° C. A solution of phenylphosphonic dichloride (6.25 g, 0.032 mol) in 30 ml. of anhydrous cyclohexane was added dropwise to the suspension over a period of 15 minutes and the resulting mixture was stirred for 0.5 hours at 0° C., then for 2.5 hours at 26° C. The reaction was quenched with the rapid addition of 6 ml. of acetic acid. The reaction mixture was concentrated in vacuo and the residue partitioned in methylene chloride and water. The layers were separated and the methylene chloride layer was washed with 5% hydrochloric acid, sodium bicarbonate, then water. The methylene chloride layer was dried over magnesium sulfate, concentrated in vacuo and the resulting residue was slurried in anhydrous diethyl ether and allowed to stand at 0° C. for 40 hours. The slurry was filtered and the resulting yellow precipitate was dissolved in a minimal amount of hot ethyl alcohol. The ethyl alcohol solution was diluted with petroleum ether to yield 1,2-diphenyl-2,3-dihydro-1H-2,1-benzazaphosphole-1-oxide as white fluffy crystals. A second crop was obtained and the combined product yield was recrystallized from ethanol to yield 1,2-diphenyl-2,3-dihydro-1H-2,1-benzazaphosphole-1-oxide (3.0 g, 33% yield) as fluffy needles having a melting point of 227°–229° C. and the following analysis:

Calculated: C, 74.74; H, 5.28; N, 4.59. Found: C, 74.62; H, 5.31; N, 4.56.

EXAMPLE 43

Under a static nitrogen atmosphere at 0° C., a solution of n-butyllithium (3.94 g, 0.0615 mol) in hexane was added to a solution of tetramethylethylenediamine (1.86 g, 0.016 mol) in 30 ml. of anhydrous cyclohexane with constant stirring. While maintaining the temperature of the reaction at 0° C., a solution of N-benzylaniline (5.5 g, 0.03 mol) in 30 ml. of anhydrous cyclohexane was added to the reaction mixture to produce a suspension containing a dilithio compound which was stirred for an additional 2 hours at 26° C. 4-Phenylphenylphosphonic dichloride (8.7 g, 0.032 mol) was directly added to this suspension followed by 60 ml. of cyclohexane. The resulting mixture was stirred for 16 hours at 26° C. The reaction was quenched with the rapid addition of a solution of acetic acid (6 g, mol) in 30 ml. of anhydrous cyclohexane. After stirring for 30 minutes, the cyclohexane layer was removed under vacuum and the resulting residue was partitioned in methylene chloride and water. The layers were separated and the methylene chloride layer was washed with water, dried over sodium sulfate and concentrated in vacuo to yield an oily residue. The oily residue was chromatographically separated on a silica gel column using ethyl acetate as the eluant. Fractions containing the benzazaphosphole were combined and concentrated in vacuo to produce a crude product. The crude product was slurried in anhydrous diethyl ether to yield 1-(4-phenylphenyl)-2-phenyl-2,3-dihydro-1H-2,1-benzazaphosphole-1-oxide (0.55 g, 5% yield) as a white solid having a melting point of 259°–261° C. and the following analysis:

Calculated: C, 78.53; H, 5.29; N, 3.67. Found: C, 78.54; H, 5.31; N, 3.64.

EXAMPLE 44

Under a static nitrogen atmosphere at 0° C., a solution of n-butyllithium (8.06 g, 0.126 mol) in hexane was added to a solution of tetramethylethylenediamine (3.71 g, 0.032 mol) in 60 ml. of anhydrous cyclohexane with constant stirring. While maintaining the temperature of the reaction at 0° C., a solution of N-benzylaniline (11 g, 0.06 mol) in 60 ml. of anhydrous cyclohexane was added to the reaction mixture to produce a suspension containing a dilithio compound. This suspension was stirred for 2 hours at 26° C. and then cooled to 0° C. in an ice bath. A solution of 3-trifluoromethylphenylphosphonic dichloride (16.8 g, 0.064 mol) in 60 ml. of anhydrous cyclohexane was added dropwise to the suspension. The ice bath was removed and the resulting mixture was stirred for 3 hours at 26° C. The reaction was quenched with the rapid addition of 12 ml. of acetic acid. The cyclohexane was removed under vacuum and the resulting residue was partitioned in methylene chloride and water. The layers were separated and the methylene chloride layer was washed with 5% hydrochloric acid, then water, dried over sodium sulfate and concentrated in vacuo to yield a brown oil. The brown oil was separated on a silica gel column using a 3:1 mixture of methylene chloride:ethyl acetate as the eluant. Fractions containing the benzazaphosphole were combined and rechromatographed using methylene chloride as the eluant. Fractions containing the benzazaphosphole were combined and concentrated in vacuo and the residue was triturated in cyclohexane to yield a white solid. The white solid was evacuated under high vacuum to remove any cyclohexane and the resulting residue was recrystallized from diethyl ether and petroleum ether to yield 1-[3-(trifluoromethyl)-phenyl]-2-phenyl-2,3-dihydro-1H-2,1-benzazaphosphole-1-oxide (6.6 g, 30% yield) as a beige solid having a melting point of 48°–51° C. and the following analysis:

Calculated: C, 64.35; H, 4.05; N, 3.75. Found: C, 64.51; H, 4.14; N, 3.60.

EXAMPLE 45

Under a static nitrogen atmosphere at 0° C., a solution of n-butyllithium (8.45 g, 0.132 mol) in hexane was added to a solution of tetramethylethylenediamine (15.3 g, 0.132 mol) in 60 ml. of anhydrous cyclohexane with constant stirring. While maintaining the temperature of the reaction at 0° C., a solution of N-trimethylsilylbenzylamine (10.8 g, 0.06 mol) in 30 ml. of anhydrous cyclohexane was added to the reaction mixture to produce a suspension containing a dilithio compound. This suspension was stirred for 16 hours at 26° C. and then was dropwise added to a solution of phenylphosphonic dichloride (12.5 g, 0.064 mol) in 120 ml. of anhydrous cyclohexane over a period of 1 hour at 26° C. After stirring for 2 hours, the reaction mixture was partitioned in methylene chloride and water. The layers were separated and the methylene chloride layer was washed with water, dried over sodium sulfate and then concentrated in vacuo to yield an oil. The oil was chromatographically separated on a silica gel column using ethyl acetate as the eluant. Fractions containing the benzazaphosphole were combined and concentrated in vacuo to produce a crude product. The crude product was crystallized from petroleum ether to yield 1-phenyl-2-(trimethylsilyl)-2,3-dihydro-1H-2,1-benzazaphosphole-1-oxide as a crystalline solid. A second crop was obtained to give a total yield of 2.45 g, 14% yield to yield 1-phenyl-2-(trimethylsilyl)-2,3-dihydro-1H-2,1-benzazaphosphole-1-oxide having a melting point of 90°–94° C. and the following analysis:

Calculated: C, 63.76; H, 6.69; N, 4.65. Found: C, 63.82; H, 6.86; N, 4.52.

EXAMPLE 46

To a solution of 1-(4-fluorophenyl)-2-phenyl-2,3-dihydro-1H-2,1-benzazaphosphole-1-oxide (1.0 g, 0.003 mol) in 25 ml. of methylene chloride was added dropwise a solution of bromine (0.8 g, 0.1 mol) in 25 ml. of methylene chloride with constant stirring. The reaction mixture was stirred for one hour and washed with water, then sodium bisulfite, again with water, dried over magnesium sulfate and concentrated in vacuo to yield a yellow solid. The yellow solid was slurried in anhydrous diethyl ether to yield 1-(4-fluorophenyl)-2-(4-bromophenyl)-2,3-dihydro-1H-2,1-benzazaphosphole-1-oxide (0.7 g, 56.4% yield) as a white solid having a melting point of 201°–205° C. and the following analysis:

Calculated: C, 57.02; H, 3.02; N, 3.50; Br, 19.97. Found: C, 56.69; H, 3.52; N, 3.46; Br, 19.85.

EXAMPLE 47

The procedure of Example 46 was employed utilizing 1,2-diphenyl-2,3-dihydro-1H-2,1-benzazaphosphole-1-oxide in lieu of 1-(4-fluorophenyl)-2-phenyl-2,3-dihydro-1H-2,1-benzazaphosphole-1-oxide to yield 1-phenyl-2-(4-bromophenyl)-2,3-dihydro-1H-2,1-benzazaphosphole-1-oxide (0.8 g, 63% yield) as a white solid having a melting point of 200°–202° C. and the following analysis:

Calculated: C, 59.40; H, 3.94; N, 3.65; Br, 20.80. Found: C, 59.50; H, 3.99; N, 3.62; Br, 20.68.

EXAMPLE 48

Under a static nitrogen atmosphere, a solution of 1,2-diphenyl-2,3-dihydro-1H-2,1-benzazaphosphole-1-oxide (1.0 g, 0.0033 mol) in 10 ml. of methylene chloride was dropwise added to a constantly stirred suspension of nitronium tetrafluoroborate (0.47 g, 0.0035 mol) in 25 ml. of methylene chloride while maintaining the temperature between −5° C. and 5° C. The reaction mixture was stirred for 3 hours at 26° C. and then added to 40 ml. of ice water. The layers were separated and the aqueous layer was extracted with methylene chloride. The methylene chloride layers were combined, dried over magnesium sulfate, and concentrated in vacuo to yield a residue which was purified on a silica gel column using ethyl acetate as the eluant. Fractions containing the benzazaphosphole were combined and concentrated in vacuo to produce a crude product. The crude product was slurried in diethyl ether to yield 1-phenyl-2-(4-nitrophenyl)-2,3-dihydro-1H-2,1-benzazaphosphole-1-oxide (0.9 g, 78% yield) as a yellow solid having a melting point of 255°–257° C. and the following analysis:

Calculated: C, 65.14; H, 4.32; N, 8.00. Found: C, 64.85; H, 4.27; N, 7.76.

EXAMPLE 49

Under anhydrous conditions, a mixture of 2-[P-ethoxy-P-methylphosphinyl]benzyl carbamic acid ethyl ester (1.2 g, 0.0025 mol) and phosphorus pentachloride (0.52 g, 0.0025 mol) in 10 ml. of carbon tetrachloride was heated at reflux for 1.5 hours. The reaction mixture was concentrated in vacuo and the resulting residue was dissolved in methylene chloride. The methylene chloride solution was washed with ice water, dried over magnesium sulfate and concentrated to produce a yellow oil. Distillation of this yellow oil at 150° C. and 0.5 torr produced an oil which solidified to yield 1-methyl-2-ethoxycarbonyl-2,3-dihydro-1H-2,1-benzazaphosphole-1-oxide as a white powder having a melting point of 102°–104° C. and the following analysis:

Calculated: C, 55.23; H, 5.90; N, 5.86. Found: C, 55.04; H, 5.96; N, 5.77.

EXAMPLE 50

A mixture of 1-phenyl-2,3-dihydro-1H-2,1-benzazaphosphole-1-oxide (1.5 g, 0.0065 mol) and methylisocyanate (1.92 g, 0.0337 mol) in 15 ml. of acetonitrile was heated with constant stirring at reflux for 16 hours. The mixture was allowed to air cool to 26° C. and was then cooled to 0° C. in an ice bath. The mixture was filtered and the precipitate washed with anhydrous ether to yield 1-phenyl-2-methylaminocarbonyl-2,3-dihydro-1H-2,1-benzazaphosphole-1-oxide (1.6 g, 86% yield) as a white solid having a melting point of 219°–221° C. and the following analysis:

Calculated: C, 62.93; H, 5.28; N, 9.79. Found: C, 62.41; H, 5.27; N, 9.65.

EXAMPLE 51

Chloroacetyl chloride (0.8 g, 0.0072 mol) was added to a suspension of 1-phenyl-2,3-dihydro-1H-2,1-benzazaphosphole-1-oxide (1.5 g, 0.00656 mol) and 1,5-diazabicyclo[5.4.0]undec-5-ene in 25 ml. of tetrahydrofuran with constant stirring. The reaction mixture was heated at reflux for 30 minutes, then stirred for 16 hours at 26° C. The reaction mixture was concentrated using a rotary evaporator and the residue was partitioned between chloroform and water. The chloroform layer was separated, and washed with 5% hydrochloric acid, a 5% sodium bicarbonate solution and then with water. The chloroform layer was dried over magnesium sulfate, concentrated in vacuo and the resulting residue was slurried in anhydrous ether to yield a crystalline solid. The crystalline solid was further purified using a silica gel column with ethyl acetate as the eluant. Fractions containing the benzazaphosphole were combined and concentrated in vacuo to produce a crude product. The crude product was slurried in diethyl ether to yield 1-phenyl-2-chloroacetyl-2,3-dihydro-1H-2,1-benzazaphosphole-1-oxide (0.9 g, 45% yield) as a solid having a melting point of 167°–169° C. and the following analysis:

Calculated: C, 58.93; H, 4.29; N, 4.58. Found: C, 58.96; H, 4.26; N, 4.58.

EXAMPLE 52

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Tables I and II is as follows:

| Plant Response | Index |
|---|---|
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
|---|---|
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

TABLE I

| Compound of Example No. | WAT | kg/h | A | B | C | D | E | F | G | H | I | J | K |
|---|---|---|---|---|---|---|---|---|---|---|---|---|---|
| 1 | 2 | 11.2 | — | 2 | 1 | 1 | 2 | 2 | 0 | 0 | 0 | 0 | 0 |
| 2 | 2 | 11.2 | — | 2 | 0 | 1 | 3 | 3 | 0 | 0 | 0 | 0 | 1 |
| 3 | 2 | 11.2 | 0 | 1 | 0 | 0 | 3 | 2 | 0 | 0 | 0 | 0 | 0 |
| 4 | 2 | 11.2 | 0 | 1 | 1 | 1 | 3 | 0 | 0 | 0 | 0 | 0 | 0 |
| 5 | 2 | 11.2 | 0 | 1 | 1 | 1 | 3 | 3 | 0 | 0 | 0 | 1 | 1 |
| 6 | 2 | 11.2 | 1 | 1 | 0 | 1 | 1 | 0 | 0 | 0 | 0 | 0 | 0 |
| 7 | 4 | 11.2 | 0 | 1 | 1 | 1 | 3 | 0 | 0 | 0 | 0 | 0 | 0 |
| 8 | 2 | 11.2 | — | 0 | 0 | 1 | 2 | 0 | 0 | 0 | 0 | 0 | 0 |
| 9 | 2 | 11.2 | 0 | 0 | 0 | 0 | 0 | 0 | 0 | 0 | 0 | 0 | 0 |
| 10 | 2 | 11.2 | 2 | 1 | 2 | — | 3 | 3 | 0 | 0 | 1 | 0 | 2 |
| 11 | 2 | 11.2 | 0 | — | 0 | 0 | 0 | 0 | 0 | 0 | 0 | 0 | 0 |
| 11 | 2 | 56.0 | 0 | 1 | 0 | 0 | 1 | 0 | 0 | 0 | 0 | 0 | 1 |
| 12 | 2 | 11.2 | 0 | 0 | 0 | 0 | 1 | 0 | 0 | 0 | 0 | 0 | 0 |
| 13 | 2 | 11.2 | — | 1 | 1 | 1 | 3 | 4 | 0 | 0 | 0 | 0 | 1 |
| 14 | 2 | 11.2 | 0 | 1 | 0 | 1 | 1 | 1 | 0 | 0 | 0 | 0 | 1 |
| 15 | 2 | 11.2 | 1 | 2 | 1 | 1 | 2 | 1 | 1 | 1 | 0 | 0 | 3 |
| 16 | 2 | 11.2 | — | 0 | 0 | 0 | 1 | 1 | 0 | — | 0 | 0 | 0 |
| 17 | 2 | 11.2 | 1 | 2 | 1 | 1 | 1 | 1 | 0 | 0 | 0 | 0 | 1 |
| 18 | 2 | 11.2 | 0 | 0 | 0 | 0 | 0 | 0 | 0 | 0 | 0 | 0 | 0 |
| 19 | 2 | 11.2 | 0 | 0 | 0 | 0 | 0 | 0 | 0 | 0 | 0 | 0 | 0 |
| 19 | 2 | 56.0 | 0 | 0 | 0 | 0 | 1 | 0 | 0 | 0 | 0 | 0 | 1 |
| 20 | 2 | 11.2 | 0 | 0 | 0 | 0 | — | 0 | 0 | 0 | 0 | 0 | 0 |
| 20 | 2 | 28.0 | 0 | 0 | 0 | 0 | 1 | 0 | 0 | 0 | 0 | 0 | 1 |
| 21 | 2 | 11.2 | 0 | — | 1 | 0 | 4 | 0 | 0 | 0 | 0 | 0 | 1 |
| 22 | 2 | 11.2 | 0 | 0 | 0 | 0 | 0 | 0 | 0 | 0 | 0 | 0 | — |
| 22 | 2 | 56.0 | 1 | 1 | 1 | 0 | 1 | 0 | 0 | 0 | 1 | 0 | 0 |
| 23 | 2 | 11.2 | 0 | 0 | 0 | 0 | 0 | 0 | 0 | 0 | 0 | 0 | 0 |

TABLE I-continued

| Compound of Example No. | WAT | kg/h | A | B | C | D | E | F | G | H | I | J | K |
|---|---|---|---|---|---|---|---|---|---|---|---|---|---|
| 23 | 2 | 56.0 | 0 | 1 | 0 | 1 | 0 | 0 | 0 | 0 | 0 | 0 | 0 |
| 24 | 2 | 11.2 | 0 | — | 0 | 0 | 0 | 0 | 0 | 0 | 0 | 0 | 0 |
| 24 | 2 | 28.0 | 0 | 1 | 0 | 1 | 1 | 0 | 0 | 0 | 0 | 0 | 0 |
| 25 | 2 | 11.2 | 0 | 0 | 0 | 0 | 0 | 0 | 0 | 0 | 0 | 0 | 0 |
| 26 | 2 | 11.2 | 0 | 0 | 0 | 0 | 0 | 0 | 0 | 0 | 0 | 0 | 0 |
| 27 | 2 | 11.2 | 0 | 0 | 0 | 0 | — | 0 | 0 | 0 | 0 | 0 | 0 |
| 27 | 2 | 56.0 | 0 | 0 | 0 | 0 | 2 | 1 | 0 | 0 | 0 | 0 | 2 |
| 28 | 2 | 11.2 | 0 | 0 | 0 | 0 | 0 | 0 | 0 | 0 | 0 | 0 | 0 |
| 28 | 2 | 56.0 | 0 | 1 | 0 | 1 | 0 | 0 | 0 | 0 | 0 | 1 | 1 |
| 29 | 2 | 11.2 | 0 | 0 | 0 | 0 | 2 | 0 | 0 | 0 | 0 | 0 | 0 |
| 30 | 2 | 11.2 | 0 | 0 | 0 | 0 | 0 | 0 | 0 | 0 | 0 | 0 | 0 |
| 30 | 2 | 56.0 | 0 | 0 | 0 | 0 | 1 | 1 | 0 | 0 | 0 | 0 | 1 |
| 31 | 2 | 11.2 | 0 | 0 | 0 | 0 | 0 | 0 | 0 | 0 | 0 | — | 0 |
| 31 | 2 | 56.0 | — | 1 | 1 | 1 | 1 | 1 | 0 | 0 | 1 | 0 | 0 |
| 32 | 4 | 11.2 | 1 | 2 | 1 | 3 | 1 | 0 | 0 | 0 | 0 | 0 | 1 |
| 32 | 2 | 11.2 | 1 | 1 | 1 | 2 | 1 | 0 | 0 | 0 | 0 | 0 | 1 |
| 33 | 2 | 11.2 | 4 | 1 | 1 | 1 | 0 | 0 | 0 | 0 | 0 | 0 | 0 |
| 34 | 2 | 11.2 | 0 | — | 0 | 0 | 0 | 0 | 0 | 0 | 0 | 0 | 0 |
| 34 | 2 | 56.0 | 0 | 1 | 0 | 0 | 1 | 0 | 0 | 0 | 0 | 0 | 0 |
| 35 | 2 | 11.2 | 0 | 0 | 0 | 1 | — | 3 | 0 | 0 | 0 | 0 | 0 |
| 36 | 2 | 11.2 | 0 | 0 | 0 | 0 | 1 | 0 | 0 | 0 | — | 0 | 0 |
| 37 | 2 | 11.2 | 0 | 0 | 0 | 0 | 0 | 0 | 0 | 0 | — | 0 | 0 |
| 38 | 2 | 11.2 | 0 | 0 | 0 | 0 | 1 | 1 | 0 | 0 | 0 | 0 | 0 |
| 39 | 2 | 11.2 | 0 | — | 0 | 0 | 0 | 0 | 0 | 0 | 0 | 0 | 0 |
| 39 | 2 | 56.0 | 0 | 2 | 1 | 1 | 0 | 1 | 0 | 0 | 0 | 0 | 0 |
| 40 | 2 | 11.2 | 0 | 1 | 0 | 1 | 2 | 1 | 0 | 0 | 0 | 0 | 0 |
| 41 | 2 | 11.2 | 0 | — | 0 | 0 | 1 | 0 | 0 | — | 0 | 0 | 0 |
| 42 | 2 | 11.2 | 0 | 0 | 0 | 0 | 0 | 0 | 0 | 0 | 0 | 0 | 0 |
| 43 | 2 | 11.2 | — | 0 | 0 | 0 | 0 | 0 | 0 | 0 | 0 | 0 | 0 |
| 44 | 2 | 11.2 | 0 | 0 | 0 | 0 | 4 | 0 | 0 | 0 | 0 | 0 | 0 |
| 45 | 2 | 11.2 | 0 | 0 | 0 | 0 | 0 | 0 | 0 | 0 | 0 | 0 | 0 |
| 46 | 2 | 11.2 | — | 0 | 0 | 0 | 4 | 0 | 0 | 0 | 0 | 0 | 0 |
| 47 | 4 | 11.2 | 0 | 0 | 0 | 0 | — | 0 | 0 | 0 | 0 | 0 | 0 |
| 47 | 2 | 28.0 | 0 | 1 | 0 | 0 | 1 | 1 | 0 | 0 | 0 | 0 | 0 |
| 48 | 2 | 11.2 | 0 | 0 | 0 | 0 | 0 | 0 | 0 | 0 | 0 | 0 | 0 |
| 49 | 2 | 11.2 | 0 | 0 | 0 | 0 | 0 | 0 | 0 | 0 | 0 | 0 | 0 |
| 49 | 2 | 56.0 | 0 | 1 | 0 | 0 | 0 | 0 | 0 | 0 | 0 | 0 | 0 |
| 50 | 2 | 11.2 | 0 | 0 | 0 | 0 | 0 | 0 | 0 | 0 | 0 | 0 | 0 |
| 50 | 2 | 56.0 | 0 | 1 | 0 | 0 | 0 | 0 | 0 | 0 | 0 | 0 | 0 |
| 51 | 2 | 11.2 | 0 | 1 | 0 | 1 | 1 | 1 | — | 0 | 0 | 0 | 0 |

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 2 | 2 | 1.12 | 0 | 0 | 0 | 0 | 0 | 0 | 1 | 0 | 0 | 4 | 1 | 0 | 0 | 0 | 0 | 0 |
| 5 | 2 | 5.6 | 1 | 2 | 1 | 0 | 0 | 1 | 1 | 2 | 4 | 4 | 4 | 1 | 0 | 1 | 1 | 1 |
| 5 | 2 | 1.12 | 0 | 0 | 0 | 0 | 0 | 0 | 0 | 0 | 0 | 3 | 3 | 0 | 0 | 0 | 0 | 0 |
| 5 | 2 | 0.28 | 0 | 0 | 0 | 0 | 0 | 0 | 0 | 0 | — | 3 | 1 | 0 | 0 | 0 | 0 | 0 |
| 10 | 2 | 5.6 | 1 | 2 | 0 | 0 | 0 | 1 | 1 | — | 1 | 3 | 2 | 2 | 0 | 0 | 0 | 2 |
| 10 | 2 | 1.12 | 1 | 0 | 0 | 0 | 0 | 1 | 1 | 1 | — | 1 | 0 | 0 | 0 | 1 | 1 | 1 |
| 10 | 2 | 0.28 | 0 | 0 | 0 | 0 | 0 | 0 | 1 | 0 | — | 1 | 1 | 0 | 0 | 0 | 0 | 0 |
| 13 | 2 | 5.6 | 1 | 1 | 0 | 0 | 1 | 1 | 1 | 2 | 4 | 3 | 3 | 2 | 0 | 1 | 1 | 2 |
| 13 | 2 | 1.12 | 1 | 1 | 0 | 0 | 0 | 0 | 1 | 0 | — | 2 | 3 | 0 | 0 | 0 | 1 | 2 |
| 32 | 2 | 5.6 | 1 | 1 | 1 | 1 | 1 | 1 | 1 | 2 | 2 | 1 | 2 | 0 | 1 | 0 | 1 | 1 |
| 32 | 2 | 1.12 | 0 | 0 | 0 | 0 | 0 | 0 | 0 | 0 | 0 | 0 | 0 | 0 | 0 | 0 | 0 | 0 |
| 35 | 2 | 5.6 | 1 | 1 | 0 | 0 | 0 | 0 | 2 | 0 | 0 | — | 2 | 0 | 0 | 0 | 1 | 1 |
| 35 | 2 | 1.12 | 1 | 0 | 0 | 0 | 0 | 0 | 0 | 0 | 0 | — | 0 | 0 | 0 | 0 | 0 | 0 |

EXAMPLE 53

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in Tables III and IV.

The pre-emergent herbicidal activity index used below is based upon average percent control of each species as follows:

| Percent Control | Index |
|---|---|
| 0-24% control | 0 |
| 25-49% control | 1 |
| 50-74% control | 2 |
| 75-100% control | 3 |

Plant species in the table are identified by the same code letters used in the previous example.

TABLE III

| Compound of Example No. | WAT | kg/h | A | B | C | D | E | F | G | H | I | J | K |
|---|---|---|---|---|---|---|---|---|---|---|---|---|---|
| 1 | 2 | 11.2 | 0 | 0 | 1 | — | 2 | 0 | 0 | 0 | 0 | 1 | 1 |
| 2 | 2 | 11.2 | 0 | 0 | 0 | 0 | 1 | 0 | 0 | 1 | 0 | 0 | 2 |
| 3 | 2 | 11.2 | 0 | 0 | 2 | 0 | 3 | 1 | 0 | 1 | 0 | 2 | 2 |
| 4 | 4 | 11.2 | 2 | 0 | 1 | — | 3 | 0 | 0 | 0 | 0 | 0 | 2 |
| 5 | 2 | 11.2 | 0 | 0 | 0 | 0 | 3 | 0 | 0 | 0 | 0 | 0 | 3 |
| 6 | 2 | 11.2 | 0 | 0 | 0 | 0 | 0 | 0 | 0 | 0 | 0 | 0 | 0 |
| 7 | 2 | 11.2 | 0 | 0 | 0 | 0 | 0 | 0 | 0 | 0 | 0 | 0 | 3 |
| 8 | 2 | 11.2 | 0 | 0 | 1 | 0 | 0 | 0 | 0 | 0 | 0 | 0 | 3 |
| 9 | 2 | 11.2 | 0 | 0 | 0 | 3 | 0 | 0 | 0 | 0 | 0 | 0 | 0 |
| 10 | 2 | 11.2 | 0 | 0 | 0 | 0 | 0 | 0 | 0 | 0 | 0 | 0 | 0 |
| 11 | 2 | 11.2 | 0 | 0 | 0 | 0 | 0 | 0 | 0 | 0 | 0 | 0 | 0 |
| 11 | 2 | 56.0 | 0 | 0 | 0 | 0 | 1 | 0 | 0 | 0 | 0 | 0 | 0 |
| 12 | 2 | 11.2 | 0 | 0 | 0 | 0 | — | 0 | 0 | 0 | 0 | 0 | 0 |
| 13 | 2 | 11.2 | 0 | 0 | 0 | 0 | 3 | 0 | 0 | 0 | 0 | 0 | — |
| 14 | 2 | 11.2 | 0 | 0 | 0 | 0 | 0 | 0 | 0 | 0 | 0 | 0 | 1 |
| 15 | 2 | 11.2 | 0 | 0 | 0 | 0 | 0 | 0 | 0 | 0 | 0 | 0 | 0 |
| 16 | 2 | 11.2 | 0 | 0 | 0 | 0 | 0 | 0 | 0 | 0 | 0 | 0 | 0 |
| 17 | 2 | 11.2 | 3 | 1 | 0 | 1 | 0 | 2 | 0 | 0 | 0 | 0 | 3 |
| 18 | 2 | 11.2 | 0 | 0 | 0 | 0 | 0 | 0 | 0 | 1 | 2 | 0 | 0 |
| 19 | 2 | 11.2 | 0 | 0 | 0 | 0 | 0 | 0 | 0 | 0 | 0 | 0 | 0 |
| 19 | 2 | 56.0 | 1 | 0 | 0 | 0 | 0 | 0 | 0 | 0 | 0 | 0 | 0 |
| 20 | 2 | 11.2 | 0 | 0 | 0 | 0 | 0 | 0 | 0 | 0 | 0 | 0 | 0 |
| 21 | 2 | 11.2 | 0 | 0 | 0 | 0 | 0 | 0 | 0 | 0 | 0 | 0 | 0 |
| 22 | 2 | 11.2 | 0 | 0 | 0 | 0 | 0 | 0 | 0 | 0 | 0 | 0 | 0 |
| 22 | 2 | 56.0 | 0 | 0 | 0 | — | 0 | 0 | 0 | 0 | 0 | 0 | 0 |
| 23 | 2 | 11.2 | 0 | 0 | 0 | 0 | 0 | 0 | 0 | 0 | 0 | 0 | 0 |
| 23 | 2 | 56.0 | 0 | 0 | 0 | 0 | 0 | 0 | 0 | 0 | 0 | 0 | 0 |
| 24 | 2 | 11.2 | 0 | 0 | 0 | — | 0 | 0 | — | 0 | 0 | 0 | 0 |
| 24 | 2 | 28.0 | 0 | 0 | 0 | 0 | 0 | 1 | 0 | 0 | 0 | 0 | 0 |
| 25 | 2 | 11.2 | 0 | 0 | 0 | 0 | 0 | 0 | 0 | 3 | 0 | 0 | 0 |
| 26 | 2 | 11.2 | — | 0 | 0 | 0 | 1 | 0 | 0 | 0 | 0 | 0 | 0 |
| 27 | 2 | 11.2 | 0 | 0 | 0 | 0 | 0 | 0 | 0 | 0 | 0 | 0 | 0 |
| 27 | 2 | 56.0 | 0 | 0 | 0 | 0 | 1 | 0 | 0 | 0 | 0 | 0 | 1 |
| 28 | 2 | 11.2 | 0 | 0 | 0 | 0 | 0 | 0 | 0 | 0 | 0 | 0 | 0 |
| 28 | 2 | 56.0 | 0 | 0 | 0 | 0 | 0 | 0 | 0 | 0 | 0 | 0 | 0 |
| 29 | 2 | 11.2 | 0 | 0 | 0 | 0 | 0 | 0 | 0 | 0 | 0 | 0 | 0 |
| 30 | 2 | 11.2 | 0 | — | 0 | 0 | 0 | 0 | 0 | 0 | 0 | 0 | 0 |
| 30 | 2 | 56.0 | 0 | 0 | 0 | 0 | 0 | 0 | 0 | 0 | 0 | 0 | 0 |
| 31 | 2 | 11.2 | 0 | 0 | 0 | 0 | 0 | 0 | 0 | 0 | 0 | 0 | 0 |
| 31 | 2 | 56.0 | 0 | 0 | 0 | 0 | 0 | 0 | 0 | 0 | 0 | 0 | 0 |
| 32 | 2 | 11.2 | 3 | 0 | 0 | 0 | 0 | 0 | 0 | 0 | 0 | 0 | 0 |
| 33 | 2 | 11.2 | 0 | 0 | 0 | 0 | 0 | 0 | 0 | 0 | 0 | 0 | 0 |
| 34 | 2 | 11.2 | 0 | 0 | 0 | — | 0 | 0 | 0 | 0 | 0 | 0 | 0 |
| 34 | 2 | 56.0 | 0 | 0 | 0 | 0 | 0 | 0 | 0 | 0 | 0 | 0 | 0 |
| 35 | 2 | 11.2 | 0 | 0 | 0 | 0 | 0 | 0 | 0 | 0 | 0 | 0 | 0 |
| 36 | 2 | 11.2 | 0 | — | 0 | 0 | 0 | 0 | 0 | 0 | 0 | 0 | 0 |
| 37 | 2 | 11.2 | 0 | 0 | 0 | 0 | 1 | 0 | 0 | 0 | 0 | 0 | 2 |
| 38 | 2 | 11.2 | 0 | 0 | 0 | 0 | 0 | 0 | 0 | 0 | 0 | 0 | 0 |
| 39 | 2 | 11.2 | 0 | 0 | 0 | 0 | 0 | 0 | 0 | 0 | — | 0 | 0 |
| 39 | 2 | 56.0 | 0 | 0 | 0 | 0 | 1 | 0 | 0 | 0 | 0 | 0 | 1 |
| 40 | 2 | 11.2 | 0 | 0 | 0 | — | 0 | 0 | 0 | 0 | 0 | 0 | 1 |
| 41 | 2 | 11.2 | 2 | 0 | 0 | 0 | 3 | 0 | 0 | 0 | 0 | 0 | 0 |
| 42 | 2 | 11.2 | 3 | 0 | 0 | 0 | 0 | 0 | 3 | 0 | 0 | 0 | 0 |
| 43 | 2 | 11.2 | 0 | 0 | 0 | 0 | 3 | 0 | 0 | 0 | 0 | 0 | 0 |
| 44 | 2 | 11.2 | 0 | 0 | 0 | 0 | 0 | 0 | 0 | 0 | 0 | 0 | 0 |
| 45 | 2 | 11.2 | 1 | 1 | 0 | 1 | 3 | 2 | 0 | 0 | 0 | 0 | 3 |
| 46 | 2 | 11.2 | 0 | 0 | 0 | 0 | 0 | 0 | 0 | 0 | 0 | 0 | 0 |
| 47 | 2 | 11.2 | 0 | 0 | 0 | 0 | 0 | 0 | 0 | 0 | 0 | 0 | 0 |
| 48 | 2 | 11.2 | 0 | 1 | 0 | 1 | 0 | 0 | 0 | 0 | 0 | 0 | 1 |
| 49 | 2 | 11.2 | 0 | 0 | 0 | 0 | 0 | 0 | 0 | 0 | 0 | 0 | 0 |
| 49 | 2 | 56.0 | 0 | 0 | 0 | 0 | 0 | 0 | 0 | 0 | 0 | 0 | 0 |
| 50 | 2 | 11.2 | 0 | 0 | 0 | 0 | 0 | 0 | 0 | 0 | 0 | 0 | 0 |
| 50 | 2 | 56.0 | 0 | 0 | 0 | 0 | 0 | 0 | 0 | 0 | 0 | 0 | 0 |
| 51 | 2 | 11.2 | 0 | 0 | 0 | 1 | 0 | 0 | 0 | 0 | 0 | 0 | 2 |

TABLE IV

| Compound of Example No. | WAT | kg/h | Plant Species | | | | | | | | | | | | | | | |
|---|---|---|---|---|---|---|---|---|---|---|---|---|---|---|---|---|---|---|
| | | | L | M | N | O | P | B | Q | D | R | E | F | C | J | S | K | T |
| 3 | 2 | 5.6 | 0 | 1 | 0 | 0 | 0 | 0 | 0 | 0 | 0 | 2 | 1 | 0 | 3 | 0 | 2 | 1 |
| 3 | 2 | 1.12 | 0 | 0 | 0 | 0 | 0 | 0 | 0 | 0 | 0 | 0 | 0 | 0 | 0 | 0 | 0 | 0 |
| 5 | 2 | 5.6 | 0 | 0 | 0 | 0 | 0 | 0 | 0 | 0 | 0 | 0 | 0 | 0 | 0 | 0 | 2 | 2 |
| 5 | 2 | 1.12 | 0 | 0 | 0 | 0 | 0 | 0 | 0 | 0 | 0 | 0 | 0 | 0 | 0 | 0 | 0 | 0 |
| 7 | 2 | 5.6 | 0 | 0 | 0 | 0 | 0 | 0 | 0 | 0 | 2 | 0 | 0 | 0 | 0 | 1 | 3 | 1 |
| 7 | 2 | 1.12 | 0 | 0 | 0 | 0 | 0 | 0 | 0 | 0 | 1 | 0 | 0 | 0 | 0 | 1 | 2 | 0 |
| 8 | 2 | 5.6 | 0 | 1 | 0 | 0 | 0 | 0 | 0 | 0 | 0 | 0 | 1 | 0 | 0 | 0 | 3 | 2 |
| 8 | 2 | 1.12 | 0 | 0 | 0 | 0 | 0 | 0 | 0 | 0 | 0 | 0 | 0 | 0 | 0 | 0 | 0 | 0 |
| 17 | 2 | 5.6 | 0 | 0 | 0 | 0 | 0 | — | 0 | 0 | 0 | 0 | 0 | 0 | 0 | 0 | 1 | 0 |
| 17 | 2 | 1.12 | 0 | 0 | 0 | 0 | 0 | 0 | 0 | 0 | — | 0 | 0 | 0 | 0 | 0 | 0 | 0 |
| 45 | 2 | 5.6 | 0 | 0 | 0 | 0 | 0 | 0 | 0 | 0 | 0 | 0 | 0 | 0 | 0 | 0 | 0 | 0 |
| 45 | 2 | 1.12 | 0 | 0 | 0 | 0 | 0 | — | 0 | 0 | 0 | 0 | 0 | 0 | 0 | 0 | 0 | 0 |

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkyl phenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific benzazaphosphole employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

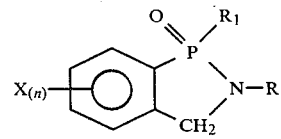

wherein R is selected from the group consisting of hydrogen, $C_1$-$C_8$ alkyl, benzyl, trimethylsilyl, phenyl, phenoxyphenyl, a

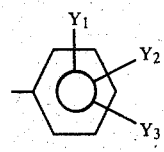

group, wherein $Y_1$ is selected from the group consisting of $C_1$-$C_4$ alkyl, $C_1$-$C_4$ alkoxy, $C_1$-$C_4$ haloalkyl, nitro and halogen and $Y_2$ and $Y_3$ are independently either hydrogen or selected from the group represented by $Y_1$, and substituted carbonyl of the formula

wherein $R_2$ is selected from the group consisting of $C_1$-$C_4$ alkoxy, $C_1$-$C_4$ haloalkyl and $C_1$-$C_4$ alkylamino; $R_1$ is selected from the group consisting of $C_1$-$C_8$ alkyl, $C_3$-$C_8$ cycloalkyl, phenyl, biphenyl, phenoxyphenyl and a

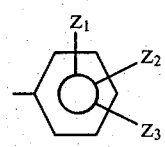

group, wherein $Z_1$ is selected from the group consisting of $C_1$-$C_4$ alkyl, $C_1$-$C_4$ alkoxy, $C_1$-$C_4$ alkylthio, $C_1$-$C_4$ dialkylamino, halogen and $C_1$-$C_4$ haloalkyl and $Z_2$ and $Z_3$ are independently hydrogen or selected from the group represented by $Z_1$; X is chloro or fluoro and n is an integer from 0 to 2; provided that when $R_1$ is methyl, R is not phenyl, phenoxyphenyl or a

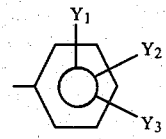

group.

2. A compound of claim 1 wherein $R_1$ is lower alkyl having from 2 to 8 carbon atoms.

3. A compound of claim 2 wherein R is phenyl or a

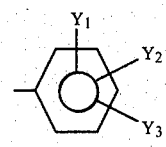

group, wherein $Y_1$ is selected from the group consisting of $C_1$-$C_4$ alkyl, $C_1$-$C_4$ alkoxy, $C_1$-$C_4$ haloalkyl, nitro and halogen and $Y_2$ and $Y_3$ are independently either hydrogen or selected from the group represented by $Y_1$.

4. A compound of claim 3 wherein $R_1$ is isopropyl.

5. A compound of claim 4 which is 1-isopropyl-2-phenyl-2,3-dihydro-1H-2,1-benzazaphosphole-1-oxide.

6. A compound of claim 4 which is 1-isopropyl-2-(m-tolyl)-2,3-dihydro-1H-2,1-benzazaphosphole-1-oxide.

7. A herbicidal composition comprising an inert adjuvant and a herbicidally effective amount of a compound of the formula

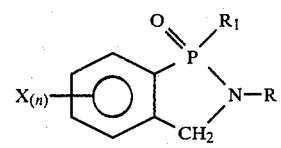

wherein R is selected from the group consisting of hydrogen, $C_1$-$C_8$ alkyl, benzyl, trimethylsilyl, phenyl, phenoxyphenyl, a

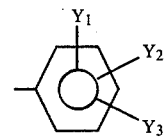

group, wherein $Y_1$ is selected from the group consisting of $C_1$-$C_4$ alkyl, $C_1$-$C_4$ alkoxy, $C_1$-$C_4$ haloalkyl, nitro and halogen and $Y_2$ and $Y_3$ are independently either hydrogen or selected from the group represented by $Y_1$, and substituted carbonyl of the formula

wherein $R_2$ is selected from the group consisting of $C_1$-$C_4$ alkoxy, $C_1$-$C_4$ haloalkyl and $C_1$-$C_4$ alkylamino; $R_1$ is selected from the group consisting of $C_1$-$C_8$ alkyl, $C_3$-$C_8$ cycloalkyl, phenyl, biphenyl, phenoxyphenyl and a

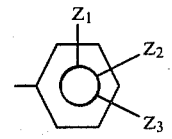

group, wherein $Z_1$ is selected from the group consisting of $C_1$-$C_4$ alkyl, $C_1$-$C_4$ alkoxy, $C_1$-$C_4$ alkylthio, $C_1$-$C_4$ dialkylamino, halogen and $C_1$-$C_4$ haloalkyl and $Z_2$ and $Z_3$ are independently hydrogen or selected from the group represented by $Z_1$; X is chloro or fluoro and n is an integer from 0 to 2; provided that when $R_1$ is methyl, R is not phenyl, phenoxyphenyl or a

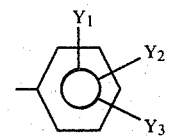

group.

8. A composition of claim 7 wherein $R_1$ is lower alkyl having from 2 to 8 carbon atoms.

9. A composition of claim 8 wherein R is phenyl or a

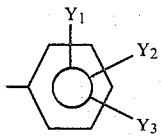

group, wherein $Y_1$ is selected from the group consisting of $C_1$–$C_4$ alkyl, $C_1$–$C_4$ alkoxy, $C_1$–$C_4$ haloalkyl, nitro and halogen and $Y_2$ and $Y_3$ are independently either hydrogen or selected from the group represented by $Y_1$.

10. A composition of claim 9 wherein $R_1$ is isopropyl.

11. A composition of claim 10 which is 1-isopropyl-2-phenyl-2,3-dihydro-1H-2,1-benzazaphosphole-1-oxide.

12. A composition of claim 10 which is 1-isopropyl-2-(m-tolyl)-2,3-dihydro-1H-2,1-benzazaphosphole-1-oxide.

13. A method of controlling undesired plants which comprises contacting said plants or the plant growth medium with a herbicidal amount of a compound of the formula

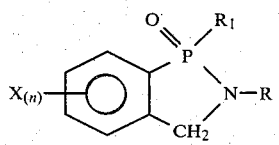

wherein R is selected from the group consisting of hydrogen, $C_1$–$C_8$ alkyl, benzyl, trimethylsilyl, phenyl, phenoxyphenyl, a

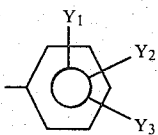

group, wherein $Y_1$ is selected from the group consisting of $C_1$–$C_4$ alkyl, $C_1$–$C_4$ alkoxy, $C_1$–$C_4$ haloalkyl, nitro and halogen and $Y_2$ and $Y_3$ are independently either hydrogen or selected from the group represented by $Y_1$, and substituted carbonyl of the formula

wherein $R_2$ is selected from the group consisting of $C_1$–$C_4$ alkoxy, $C_1$–$C_4$ haloalkyl and $C_1$–$C_4$ alkylamino; $R_1$ is selected from the group consisting of $C_1$–$C_8$ alkyl, $C_3$–$C_8$ cycloalkyl, phenyl, biphenyl, phenoxyphenyl and a

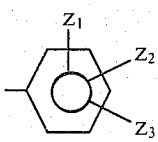

group, wherein $Z_1$ is selected from the group consisting of $C_1$–$C_4$ alkyl, $C_1$–$C_4$ alkoxy, $C_1$–$C_4$ alkylthio, $C_1$–$C_4$ dialkylamino, halogen and $C_1$–$C_4$ haloalkyl and $Z_2$ and $Z_3$ are independently hydrogen or selected from the group represented by $Z_1$; X is chloro or fluoro and n is an integer from 0 to 2; provided that when $R_1$ is methyl, R is not phenyl, phenoxyphenyl or a

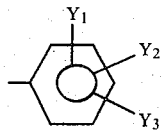

group.

14. A method according to claim 13 wherein $R_1$ is lower alkyl having from 2 to 8 carbon atoms.

15. A method according to claim 14 wherein R is phenyl or a

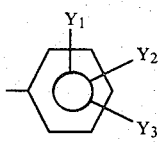

group, wherein $Y_1$ is selected from the group consisting of $C_1$–$C_4$ alkyl, $C_1$–$C_4$ alkoxy, $C_1$–$C_4$ haloalkyl, nitro and halogen and $Y_2$ and $Y_3$ are independently either hydrogen or selected from the group represented by $Y_1$.

16. A method according to claim 15 wherein $R_1$ is isopropyl.

17. A method according to claim 16 wherein the compound is 1-isopropyl-2-phenyl-2,3-dihydro-1H-2,1-benzazaphosphole-1-oxide.

18. A method according to claim 16 wherein the compound is 1-isopropyl-2-(m-tolyl)-2,3-dihydro-1H-2,1-benzazaphosphole-1-oxide.

19. A process for producing a compound of the formula

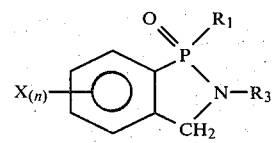

wherein $R_1$ is selected from the group consisting of $C_1$–$C_8$ alkyl, $C_3$–$C_8$ cycloalkyl, phenyl, biphenyl, phenoxyphenyl and a

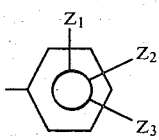

group, wherein $Z_1$ is selected from the group consisting of $C_1$–$C_4$ alkyl, $C_1$–$C_4$ alkoxy, $C_1$–$C_4$ alkylthio, $C_1$–$C_4$ dialkylamino, halogen, and $C_1$–$C_4$ haloalkyl and $Z_2$ and $Z_3$ are independently hydrogen or selected from the group represented by $Z_1$; $R_3$ is selected from the group consisting of $C_1$–$C_8$ alkyl, benzyl, trimethylsilyl, phenyl, phenoxyphenyl and a

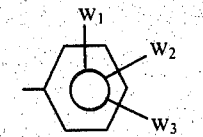

group, wherein $W_1$ is selected from the group consisting of $C_1$-$C_4$ alkyl, $C_1$-$C_4$ alkoxy, $C_1$-$C_4$ haloalkyl, fluoro and chloro and $W_2$ and $W_3$ are independently either hydrogen or selected from the group represented by $W_1$; X is chloro or fluoro; and n is an integer from 0 to 2; which comprises (a) forming an admixture of a N-benzylamine of the formula

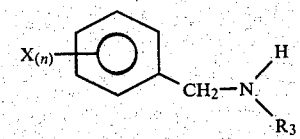

wherein $R_3$, X and n are above defined; in a solvent selected from the class consisting of benzene and liquid alkanes, with an organolithium compound in the presence of a tertiary diamine at a temperature between $-80°$ C. and $26°$ C. to produce a dilithio compound of the formula

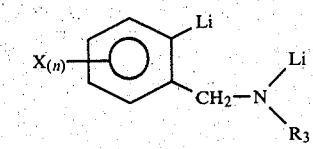

wherein X, n and $R_3$ are above defined; and then (b) reacting the dilithio compound with a phosphonic dichloride of the formula

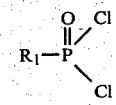

wherein $R_1$ is above defined; at a temperature between $-80°$ C. and $26°$ C.

20. A process according to claim 19 wherein the reaction between the dilithio compound and the substituted phosphonate is conducted at a temperature between $-76°$ C. and $-65°$ C.

21. A process according to claim 19 wherein the organolithium compound is t-butyllithium.

22. A process according to claim 19 wherein the tertiary diamine is N,N,N',N'-tetramethylethylenediamine.

* * * * *